(12) United States Patent
Schader (10) Patent No.: US 10,238,809 B2
(45) Date of Patent: Mar. 26, 2019

(54) SAFETY DEVICE FOR A DRUG DELIVERY DEVICE

(71) Applicant: Sanofi-Aventis Deutschland GMBH, Frankfurt-am-Main (DE)

(72) Inventor: Marc Schader, Frankfurt am Main (DE)

(73) Assignee: Sanofi-Aventis Deutchland GMBH, Frankfurt am Main (DE)

( * ) Notice: Subject to any disclaimer, the term of this patent is extended or adjusted under 35 U.S.C. 154(b) by 60 days.

(21) Appl. No.: 15/105,247

(22) PCT Filed: Dec. 18, 2014

(86) PCT No.: PCT/EP2014/078548
§ 371 (c)(1),
(2) Date: Jun. 16, 2016

(87) PCT Pub. No.: WO2015/091847
PCT Pub. Date: Jun. 25, 2015

(65) Prior Publication Data
US 2016/0317754 A1    Nov. 3, 2016

(30) Foreign Application Priority Data
Dec. 20, 2013 (EP) .................................. 13199019

(51) Int. Cl.
*A61M 5/32* (2006.01)
(52) U.S. Cl.
CPC .......... *A61M 5/3202* (2013.01); *A61M 5/326* (2013.01); *A61M 5/3245* (2013.01);
(Continued)

(58) Field of Classification Search
CPC ........ A61M 5/3243; A61M 2005/3247; A61M 2005/3267; A61M 5/3202; A61M 5/3204;
(Continued)

(56) References Cited

U.S. PATENT DOCUMENTS 5,336,199 A * 8/1994 Castillo ............... A61M 5/3243
128/919
5,415,645 A * 5/1995 Friend ................... A61M 5/326
604/110
(Continued)

FOREIGN PATENT DOCUMENTS

| JP | 2009-506815 | 2/2009 |
| WO | WO01/76665 | 10/2001 |
| WO | WO 2007/026163 | 3/2007 |

OTHER PUBLICATIONS

International Search Report and Written Opinion in International Application No. PCT/EP2014/078548, dated Apr. 29, 2015, 11 pages.
(Continued)

*Primary Examiner* — Quynh-Nhu H. Vu
(74) *Attorney, Agent, or Firm* — Fish & Richardson P.C.

(57) ABSTRACT

The invention relates to a safety device (S) for a drug delivery device (1), comprising: —a support body (2) adapted to receive and hold the drug delivery device (1), —a needle shield (8) slidably arranged relative to the support body (2), —an inner locking mechanism (12) arranged inside the needle shield (8) between a front end of the needle shield (8) and a front end of the support body (2) and adapted to lock and unlock the needle shield (8).

18 Claims, 4 Drawing Sheets

(52) U.S. Cl.
CPC ......... *A61M 5/3204* (2013.01); *A61M 5/3287* (2013.01); *A61M 2005/3247* (2013.01); *A61M 2005/3267* (2013.01)

(58) Field of Classification Search
CPC ... A61M 5/3245; A61M 5/326; A61M 5/3287
See application file for complete search history.

(56) References Cited

U.S. PATENT DOCUMENTS

| | | | | |
|---|---|---|---|---|
| 7,147,624 | B2* | 12/2006 | Hirsiger | A61M 5/326 604/198 |
| 2008/0249477 | A1* | 10/2008 | Paproski | A61M 5/326 604/198 |
| 2008/0269691 | A1 | 10/2008 | Cowe | |
| 2011/0021988 | A1* | 1/2011 | Jensen | A61M 5/326 604/110 |
| 2011/0160675 | A1 | 6/2011 | Ruan et al. | |
| 2011/0288491 | A1 | 11/2011 | Newman et al. | |
| 2012/0316508 | A1* | 12/2012 | Kirchhofer | A61M 5/31553 604/198 |
| 2014/0052071 | A1* | 2/2014 | Pickhard | A61M 5/288 604/192 |
| 2014/0303564 | A1* | 10/2014 | Roberts | A61M 5/326 604/198 |
| 2015/0038922 | A1* | 2/2015 | Slemmen | A61M 5/326 604/263 |

OTHER PUBLICATIONS

International Preliminary Report on Patentability in International Application No. PCT/EP2014/078548, dated Jun. 21, 2016, 8 pages.
Rote Liste, "50. Hypophysen-, Hypothalamushormone, andere regulatorische Peptide u. ihre Hemmstoffe," Chapter 50, ed. 2008, 20 pages.

* cited by examiner

SAFETY DEVICE FOR A DRUG DELIVERY DEVICE

CROSS-REFERENCE TO RELATED APPLICATIONS

This application is a U.S. national stage application under 35 USC § 371of International Application No. PCT/EP2014/078548, filed on Dec. 18, 2014, which claims priority to European Patent Application No. 13199019.4, filed on Dec. 20, 2013, the entire contents of which are incorporated herein by reference.

TECHNICAL FIELD

The invention relates to a safety device for a drug delivery device

BACKGROUND OF THE INVENTION

Many drug delivery devices of the prior art, such as auto-injectors or syringes, have been developed for self-administration of a drug. Such drug delivery devices comprise a pre-mounted needle to ease the self-administration of the drug. In order to keep the needle sterile, the needle and the distal end of the syringe connected to the needle are covered with a needle cap made of a flexible material such as rubber.

To protect the needle of the drug delivery device from damage or to protect people from needle-stick injuries prior to use of the device, the needle cap can be encased by a protective needle shield made of a material that is more rigid than the material of the needle cap, as for example a rubber needle cap.

In order to prepare the drug delivery device for delivering a dose the needle cap and if necessary the protective needle shield have to be removed from the needle. This may be done by gripping the needle cap or the encasing protective needle shield and pulling it/them away from the needle. This will usually result in a removal of the needle cap as well.

SUMMARY OF THE INVENTION

Certain aspect of the present invention relate to a safety device which supports an easy, reliable and safe removal of a needle cap from a syringe as well as a permanent needle safety after drug delivery. Certain aspect of the present invention relate to a drug delivery device with an improved safety device.

Exemplary embodiments of the invention are given in the dependent claims.

The invention allows that in the case of an incorrect removal of the needle cap out off the drug delivery device, and thus if the drug delivery device is misused during its preparing and activation for delivery, the drug delivery device is protected against an incorrect use by an inner locking mechanism. Further, after drug delivery the invention allows a safe lock of the needle shield to permanently cover the needle by the needle shield which is fixed by the inner locking mechanism as well as to permanently protect the used drug delivery device against a re-use.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
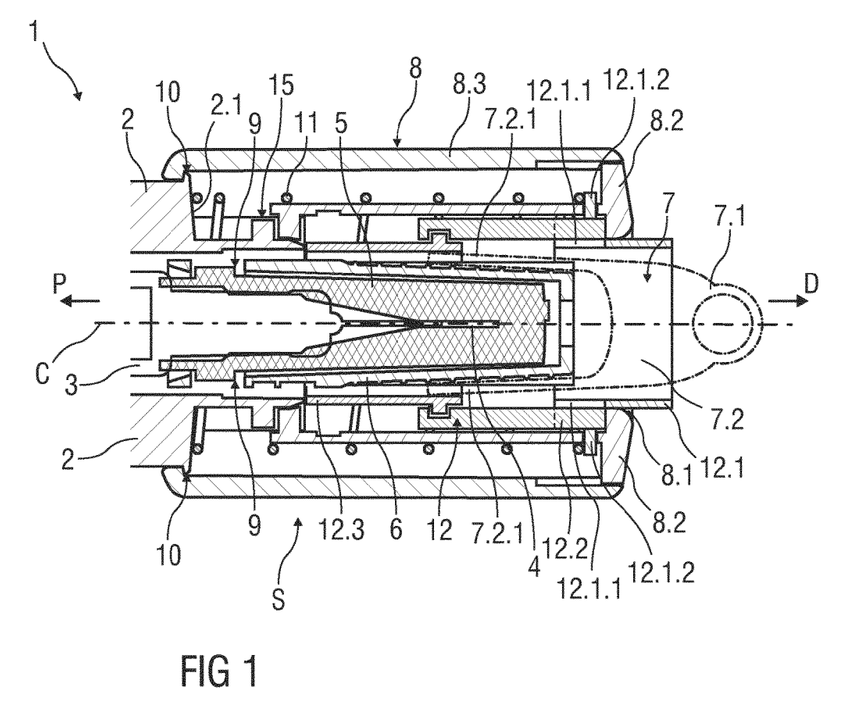
FIG. 1 is a partial longitudinal section of a drug delivery device with an exemplary embodiment of an improved safety device with an inner locking mechanism.

FIG. 1 is a partial view of a drug delivery device 1 comprising a support body 2 forming part of a housing and a safety device S, in particular a needle safety device protecting the drug delivery device 1 against misuse and re-use.

The drug delivery device 1 could be an auto-injector with a container, an injection pen or a syringe, e.g. a pre-filled syringe, or another medicament container or any other application with comparable functional principle.

The support body 2 is designed as a syringe carrier. In particular, the support body 2 may be designed as a one part or multiple part housing or carrier, e.g. the support body may comprise a back part and a front part.

In the context of this description, the term "back" or "proximal" end of a component or of a device refers to the end closest to the user's hand or furthest away from the delivery or injection site. A direction toward said proximal end is denoted as proximal direction P. The term "front" or "distal" end of a component or device refers to the end furthest from the user's hand or closest to the delivery or injection site. A direction toward said distal end is denoted as distal direction D.

In an exemplary embodiment, the support body 2 is adapted to receive, hold and encase a syringe 3 with a pre-mounted needle 4. The syringe 3 may be a pre-filled syringe pre-filled with a drug. The needle 4 is substantially aligned with a central axis C of the drug delivery device 1.

The needle 4 may be fixed. Alternatively, the needle 4 may be removable from the syringe 3, as a matter of design choice.

The needle 4 is covered by a needle cap 5 that maintains the sterile condition of the needle 4 and of the content of the syringe 3. The needle cap 5 is adapted to house and cover the needle 4 before use to protect it against damages during transport or travel and to keep it sterile until injection starts. The needle cap 5 is made of a flexible material such as rubber. In particular the needle cap 5 is formed as an inner rubber needle shield or a soft rubber or rubber like core for easier and safer handling. It is fitted to the distal part of the syringe 3 e.g. by friction.

For mechanical protection, the needle cap 5 may be encased by a so called rigid needle shield (shortly named RNS).

In the exemplary embodiment according to FIG. 1, a protective needle shield 6 entirely encases the needle cap 5 and a distal part of the syringe 3. The protective needle shield 6 is formed as a rigid, in particular a plastic needle shield, the so-called rigid needle shield. In particular, the protective needle shield 6 may be formed as a cylinder with e.g. a circular or polygonal cross-section and aligned with the central axis C with an open distal and an open proximal ending.

For removing the needle cap 5 as well as the protective needle shield 6 from the needle 4 and the syringe 3, a needle cap remover 7 is provided. The function and the arrangement of the needle cap remover 7 directly onto the needle cap 5 or onto the protective needle shield 6 encasing the needle cap 5 are identical and do not differ from each other. Thus, the following description regarding a needle cap remover 7 arranged onto the rigid protective needle shield 6 encasing the needle cap 5 applies also to a needle cap remover directly arranged onto the needle cap without an encasing.

The needle cap remover 7, the protective needle shield 6 and the needle cap 5 are adapted to be connected to each other by a friction fit and/or by positive locking and/or by a form-fit.

For mechanical protection of the needle 4 after removal of the protective needle shield 6 as well as of the needle cap 5 before and after drug delivery, the drug delivery device 1 further comprises a needle shield 8.

To remove the needle cap 5 a force is required that overcomes the static friction between the flexible material of the needle cap 5, for example rubber, and the material of the syringe, for example thermoplastic or glass. Therefore, the protective needle shield 6 is non-positively and/or positively locked to the needle cap 5 by interlocking fasteners 9 such as snap-in fasteners, plugs and cooperating recesses, pins and grooves.

During removal, the needle cap remover 7 grips the protective needle shield 6 in such a manner that the protective needle shield 6 together with the needle cap 5 is pulled off the syringe 3.

In a possible shown embodiment, the needle cap remover 7 comprises at least an outer grip 7.1 protruding from a front surface 8.2 of the needle shield 8 to allow gripping by a user to pull off the protective needle shield 6 as well as the needle cap 5 from the drug delivery device 1 and an inner grip 7.2 adapted to grip the outer surface of the protective needle shield 6.

In an exemplary embodiment, the inner grip 7.2 comprises at least one grip arm 7.2.1 inwardly protruding through an opening 8.1 of the front surface 8.2 of the needle shield 8 and adapted to be assembled onto the protective needle shield 6 by pressing them into and through the opening 8.1.

Alternatively or additionally, it is also possible to have a plurality of radially protruding grip arms 7.2.1, such as arms in particular arranged rotationally symmetric around the central axis C through the centre of the needle shield 8. In a further not shown embodiment, the grip arm 7.2.1 can have a cylindrical shape with a structural inner surface to grip the outer surface of the protective needle shield 6.

FIG. 1 illustrates, that the needle shield 8 is mounted on the support body 2 of the drug delivery device 1 in a movable manner by a snap-fit connection 10. The needle shield 8 is adapted to cover the needle 4 before and after injection, wherein the needle shield 8 comprises a needle shield end, in particular the front surface 8.2 adapted to engage an injection site.

As a matter of design choice, the needle shield 8 may be designed as one part or in multiple parts wherein the front surface 8.2 may be designed as one part separated from a lateral surface 8.3 encasing the needle 4. Furthermore, the needle shield 8 comprises flexible arms 8.4 protruding inwardly and adapted to ensure the needle safety before and after use of the drug delivery device 1.

In an exemplary embodiment the support body 2 is formed as a cylinder with an open distal end with a circumferential edge 2.1. The open distal end of the support body 2 is arranged concentrically between the needle shield 8 and the protective needle shield 6. The circumferential edge 2.1 is formed such that the outer perimeter of the support body 2 is reduced. The support body 2 and the needle shield 8 are movable relative to each other. In an exemplary embodiment a pin-slot guidance 15 is provided wherein one of the support body 2 and the needle shield 8 comprises a guide pin and the other comprises the guide slot or otherwise.

A spring 11 is arranged to bias the support body 2, in particular the circumferential edge 2.1, relative to an inner locking mechanism 12, in particular another circumferential edge 12.1.2.

The inner locking mechanism 12 as well as the needle shield 8 and the support body 2 are parts of the safety device S to cover the needle 4 before, during and after drug delivery as well as to protect the drug delivery device 1 against misuse and reuse.

In an exemplary embodiment the inner locking mechanism 12 is arranged inside the needle shield 8 between a front end of the needle shield 8 and a front end of the support body 2. The inner locking mechanism 12 is adapted to prevent premature activation of the needle safety feature as the drug delivery device 1 is not usable afterwards by an incorrect user operation.

In an exemplary embodiment, the separate inner locking mechanism 12 comprises at least three independent locking parts 12.1 to 12.3. The two outer ones of the three locking parts 12.1 and 12.3 are telescopably movable relative to the middle locking part 12.2, wherein the middle locking part 12.2 relatively rotates to the others. In particular, the two outer locking parts 12.1 and 12.3 are arranged at the outer end of the middle locking part 12.2 and are adapted to move towards each other.

FIGS. 2A to 2D show views of a drug delivery device 1 in different states.

Figure 2A:
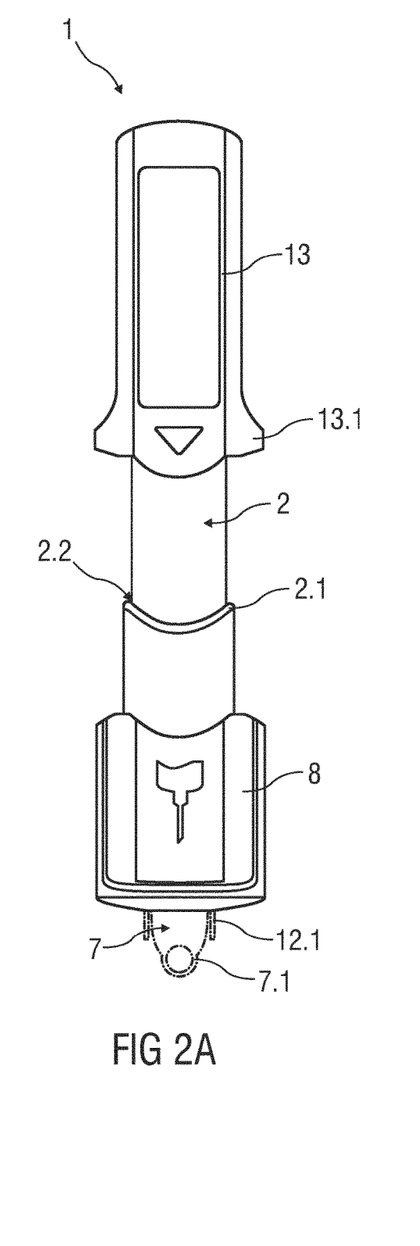
FIGS. 2A to 2D show views of a drug delivery device in different states.

In particular, FIG. 2A shows the drug delivery device 1 in a delivery state. The drug delivery device 1 comprises at least a support body 2 formed as a one part body (as it is shown) or as a two part body with a front body and a rear body, a needle shield 8 and an outer cap 13 forming part of a not shown plunger and suitable for manual gripping with a gripping flange 13.1. The shape of the outer cap 13 can vary, e.g. may be a generally cylindrical form or oval form.

If the drug delivery device 1 is held at the needle shield 8 and thus misused during removal of the needle cap 5 by removing of the needle cap remover 7, the inner locking mechanism 12 is adapted to prevent premature activation of the needle safety function and to lock the needle shield 8 as the drug delivery device 1 is not usable afterwards so that the drug delivery device 1 cannot perform the following insertion and injection/delivery steps anymore, in particular an incorrect injection is prevented.

In particular, the inner locking mechanism 12 is adapted to secure and hold the needle shield 8 and the support body 2 relatively to each other in such a manner that a premature activation of the needle safety function is prevented during removing of the needle cap 5.

In the case of an incorrect operation or an incorrect pulling out of the needle cap 5 the drug delivery device 1 is further usable due to the inner locking mechanism 12 if the user pushes the needle shield 8 on the delivery site.

To correctly remove the protective needle shield 6 as well as the needle cap 5 the drug delivery device 1 should be held at the outer cap 13 so that the inner locking mechanism 12 is locked until the drug delivery device 1 is ready for insertion.

Figure 2B:
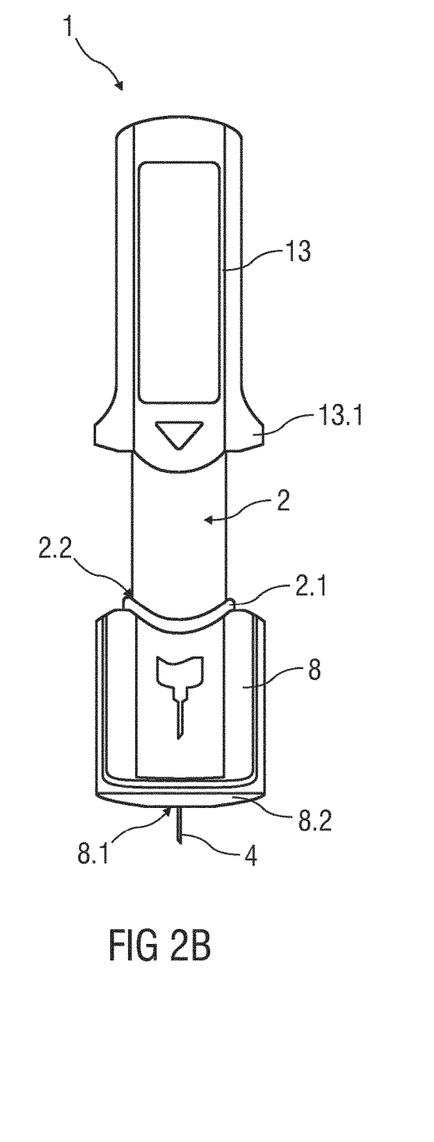

FIG. 2B shows the drug delivery device 1 placed onto a delivery site with the needle 4 which may be inserted into the delivery site.

The outer locking part 12.3 is pushed into the needle shield 8 if the drug delivery device 1 is placed onto the delivery site. By pressing the drug delivery device 1 further onto the delivery site, the outer cap 13 pushes the support body 2 and thus the syringe 3 with the fixed needle 4 into the needle shield 8 until the proximal end of the needle shield 8 hits an outer edge 2.2 of the support body 2 so that the needle 4 protrudes through the opening 8.1.

Figure 2C:
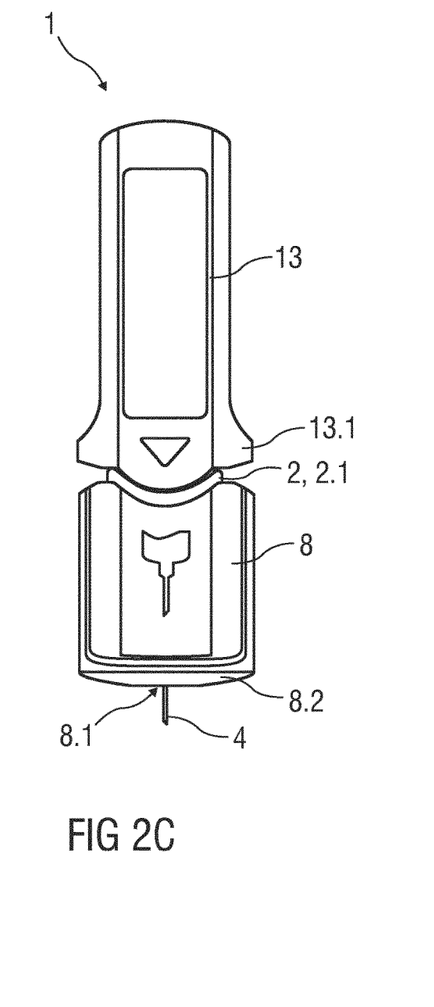

FIG. 2C shows the drug delivery device 1 after delivery of the drug but before the drug delivery device 1 is removed from the delivery site so that the needle 4 further protrudes through the opening 8.1. During delivery of the drug the outer cap 13 moves in the distal direction D and pushes a not shown plunger movably arranged inside the syringe 3 in the distal direction D until the outer cap 13 hits an inner edge 2.3 of the support body 2 and the inner plunger hits the distal end of the syringe 3 so that the drug is delivered.

Figure 2D:
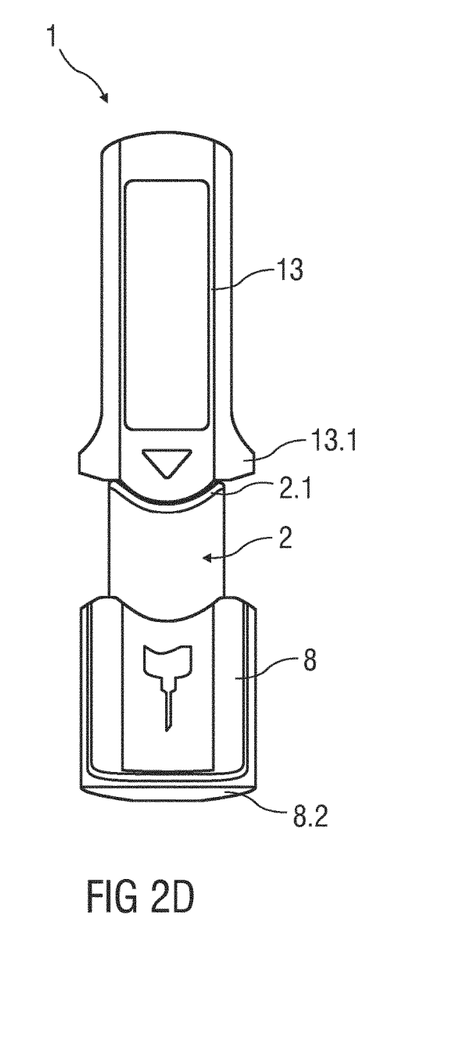

FIG. 2D shows the drug delivery device 1 after delivery of the drug and after the drug delivery device 1 is removed from the delivery site so that the needle 4 is covered by the needle shield 8.

Due to the spring 11 biasing the support body 2 relative to the inner locking mechanism 12, the support body 2 and the needle shield 4 are pushed apart during removal of the drug delivery device 1 from the delivery site. The inner locking mechanism 12 is adapted to permanently lock the needle shield 8 and the support body 2 in such a manner that the needle 4 is safely and permanently covered by the needle shield 8.

Figure 3A:
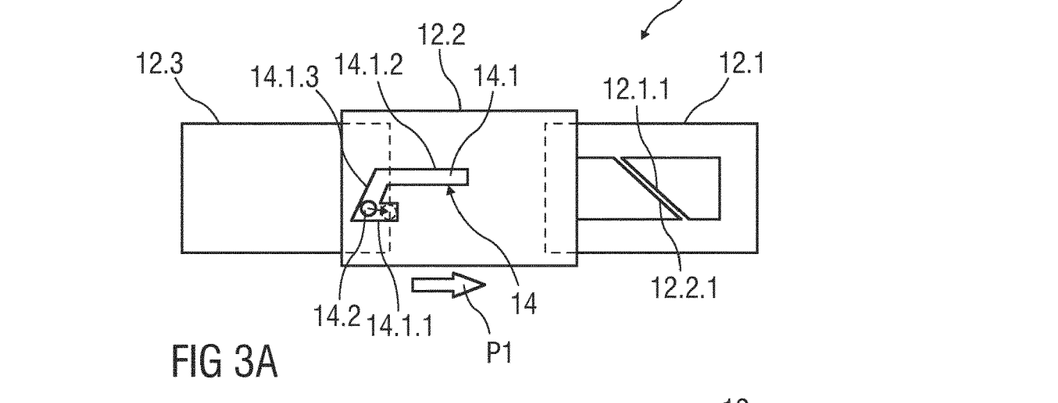
FIGS. 3A to 3C show partial longitudinal sections of an exemplary embodiment of an inner locking mechanism of a safety device in different states.
Figure 3B:
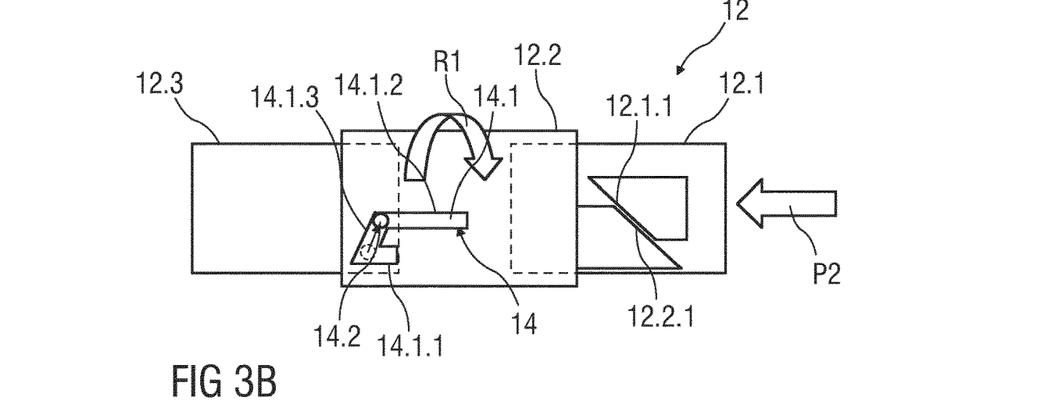
Figure 3C:
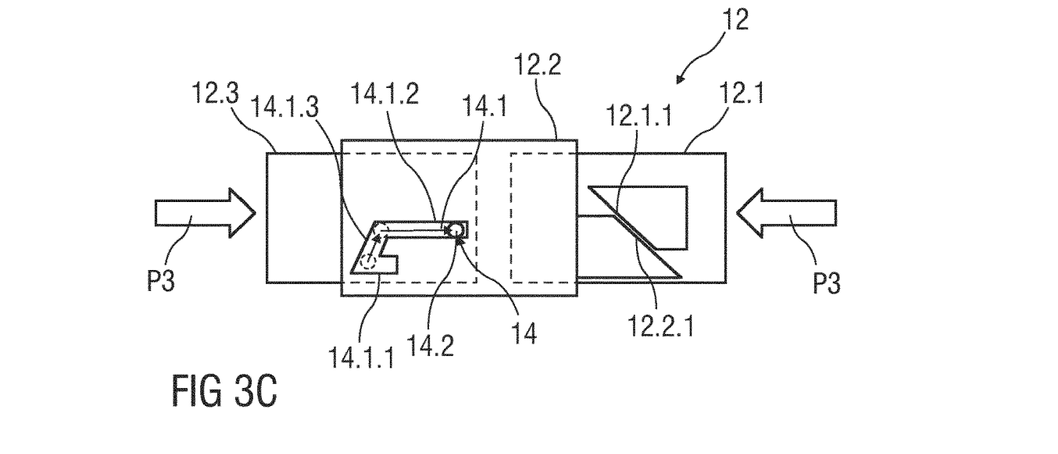

FIGS. 3A to 3C show partial longitudinal sections of an exemplary embodiment of an inner locking mechanism 12 of a safety device S in different states.

FIG. 3A shows the inner locking mechanism 12 in a delivery state of the drug delivery device 1 with an assembled needle cap remover 7 as it is shown in FIG. 1.

Two of the three locking parts 12.1 and 12.2, in particular one of the outer locking parts 12.1 and the middle locking part 12.2 comprise corresponding angled guiding surfaces 12.1.1 and 12.2.1 adapted to rotate at least the middle locking part 12.2 relative to the other outer locking parts 12.1 and 12.3 on telescoping movement thereof towards each other. In particular, the guiding surfaces 12.1.1 and 12.2.1 are angled with respect to a longitudinal axis of the inner locking mechanism 12 and in opposite directions.

Additionally, another two of the three locking parts 12.2 and 12.3, in particular the other outer locking part 12.3 and the middle locking part 12.2 are telescopably and rotatably movable relative to each other by a pin-slot guidance 14 wherein the middle locking part 12.2 rotates.

In an exemplary embodiment, the pin-slot guidance 14 comprises a guide track 14.1 and a corresponding guide pin 14.2. The guide track 14.1 may be formed into the wall of one of the locking parts 12.1 to 12.3, in particular into the wall of the middle locking part 12.2. In a possible embodiment, the guide track 14.1 comprises two longitudinal sections 14.1.1 and 14.1.2 arranged at each end of the guide track 14.1 and a middle section 14.1.3 angled with respect to a longitudinal axis of the inner locking mechanism 12 and connecting the two longitudinal sections 14.1.1 and 14.1.2.

The guide pin 14.2 is part of one of the other locking parts 12.1 to 12.3, in particular of the outer locking part 12.3.

In a further embodiment, the middle section 14.1.3 of the guide track 14.1 and/or the angled guiding surfaces 12.1.1 and 12.2.1 have an angle from 35° to 65°, in particular of 45° and 65°.

In use of the drug delivery device 1, the needle cap remover 7 is pulled out of the opening 8.1 of the drug delivery device 1. Due to the coupling of the needle cap remover 7, the protective needle shield 6 and the needle cap 5 are removed from the needle 4 when the needle cap remover 7 is removed from the drug delivery device 1.

Due to the design of the inner locking mechanism 12 the drug delivery device 1 can only be used if the outer cap 13 is gripped during removal of the needle cap 5 as it is described above. In particular, the outer locking parts 12.1 and 12.3 remain in their delivery positions so that the inner locking mechanism 12 is locked but not permanently locked.

If the drug delivery device 1 is misused during activation for delivery, in particular if the needle shield 8 is gripped during removal of the needle cap 5, due to a friction fit between the needle cap remover 7 and the outer locking part 12.3 the outer locking part 12.3 is slightly moved into the distal direction D as it is shown by an arrow P1 so that the guide pin 14.2 snaps into the distal end of the longitudinal section 14.1.1. Hence, the inner locking mechanism 12 prevents a premature activation and the needle 4 is covered by the needle shield 8 if the protective needle cap 5 is incorrectly pulled out off the drug delivery device 1.

If the drug delivery device 1 is correctly held at the outer cap 13 during removal of the needle cap 5 the outer cap 13, the support body 2 fixed to the outer cap 13 as well as the outer locking part 12.3 attached to the support body 2 remain in their delivery position or state and thus the guide pin 14.2 remains in its delivery position and thus in a locking position at the beginning of the middle section 14.1.3 of the guide track 14 in which the needle shield 8 is secured and thus locked against moving.

However, the other outer locking part 12.1 at the distal end of the drug delivery device 1 may be slightly moved out of the opening 8.1 and the drug delivery device 1 is ready for insertion and injection.

FIG. 3 B shows the inner locking mechanism 12 after removal of the needle cap 5 and during placing the drug delivery device 1 with its needle shield end, in particular the front surface 8.2 onto the injection or delivery site to perform an injection.

During placing the drug delivery device 1 onto the delivery site the outer locking part 12.1 is pushed inwards according to arrow P2. Due to its corresponding angled guiding surfaces 12.1.1 and 12.2.1 and the pin-slot guidance 14 the outer and the middle locking parts 12.1 and 12.2 are telescopably and rotatably movable relative to each other according to arrow P2 and arrow R1 so that the guide pin 14.2 moves to the other end of the middle section 14.1.3 of the guide track 14 to unlock the needle shield 8.

Hence, during activation movement of the drug delivery device 1 the outer locking part 12.1 serves as a user interface or a button on the front or top end of the needle shield 8. With other words: When pressing the outer locking part 12.1 onto the delivery site the outer locking part 12.1 is pushed inwards in the proximal direction P and the rotating mechanism will be twisted, in particular the middle locking part 12.2 rotates relatively to the outer locking parts 12.1, 12.3 so that the needle shield 8 will be unlocked when the guide pin 14.2 reaches the opposite end of the middle section 14.1.3.

FIG. 3C shows the inner locking mechanism 12 during and after insertion of the needle 4. Due to unlocking of the needle shield 8 and pushing of the outer cap 13 to perform a needle insertion the support body 2 and thus the attached outer locking part 12.3 are movable relative to the needle shield 8 into the distal direction D. The slot-pin guidances 14 and 15 guide the movement of the internal locking mechanism 12 as well as of the support body 2 relative to the needle shield 8. More particularly, the outer locking part 12.3 and the middle locking part 12.2 are moveable relative to each other and relative to the needle shield 8 into the distal direction D according to arrow P3 until the guide pin 14.2 reaches the distal end of the longitudinal section 14.1.2. Hence, the spring 11 is tensioned.

After drug delivery when the drug delivery device 1 is removed from the delivery site the needle shield 8 is pushed in its advanced position to cover the needle 4 by the spring force of spring 11. In particular, the support body 2 and the needle shield 8 are pushed apart. Furthermore, the needle shield 8 and the support body 2 are locked to each other by the flexible arms 8.4 in such a manner that the needle 4 is safely and permanently covered by the needle shield 8.

The needle safety after use of the drug delivery device 1 is realized by the flexible arms 8.4 of the needle shield 8. The flexible arms 8.4 are guided in a so called "J-track" wherein if the flexible arms 8.4 reach a defined end position in the "J-track" the needle shield 8 is fixed after use.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 drug delivery device
2 support body
2.1 circumferential edge
2.2 outer edge
2.3 inner edge
3 syringe
4 needle
5 needle cap
6 protective needle shield
7 needle cap remover
7.1 outer grip
7.2 inner grip
7.2.1 inner grip arm
8 needle shield
8.1 opening
8.2 front surface
8.3 lateral surface
9 interlocking fasteners
10 snap-fit connection
11 spring
12 inner locking mechanism
12.1-12.3 locking parts
12.1.1, 12.2.1 angled guiding surface
12.1.2 circumferential edge
13 outer cap
13.1 gripping flange
14 pin-slot guidance
14.1 guide track
14.1.1, 14.1.2 longitudinal section
14.1.3 middle section
14.2 guide pin
15 further pin-slot guidance
C central axis
D distal direction
P proximal direction
P1-P3, R1 arrow
S safety device

The invention claimed is:

1. A safety device for a drug delivery device, comprising:
   a support body adapted to receive and hold the drug delivery device,
   a needle shield slidably arranged relative to the support body,
   an inner locking mechanism arranged inside the needle shield between a front end of the needle shield and a front end of the support body and adapted to lock and unlock the needle shield,
   wherein the inner locking mechanism comprises at least three independent locking parts, and
   wherein two outer locking parts of the at least three independent locking parts are telescopically movable relative to a middle locking part of the at least three independent locking parts.

2. The safety device according to claim 1, wherein the two outer locking parts are arranged respectively and oppositely at outer ends of the middle locking part and are adapted to move towards each other.

3. The safety device according to claim 1, wherein two of the three independent locking parts comprise corresponding angled guiding surfaces adapted to rotate at least one of the at least three independent locking parts relative to the other on telescoping movement thereof towards each other.

4. The safety device according to claim 3, wherein the guiding surfaces are angled with respect to a longitudinal axis of the inner locking mechanism and in opposite directions.

5. The safety device according to claim 4, wherein the middle section and/or the angled guiding surfaces have an angle from 35° to 65°.

6. The safety device according to claim 3, wherein the at least one of the three independent locking parts is telescopically and rotatably movable relative to the other by a pin-slot guidance.

7. The safety device according to claim 6, wherein the pin-slot guidance comprises two longitudinal sections arranged at each end of the pin-slot guidance and a middle section angled with respect to a longitudinal axis of the inner locking mechanism and connecting the two longitudinal sections.

8. The safety device according to claim 6, wherein the pin-slot guidance comprises a guide track and a corresponding guide pin, wherein the guide track is formed into the wall of one of the at least three independent locking parts, and wherein the guide pin is part of one of the other of the at least three independent locking parts.

9. The safety device according to claim 8, wherein the guide pin is part of the outer locking part.

10. The safety device according to claim 8, wherein the guide track is formed into the wall of the middle locking part.

11. The safety device according to claim 1, wherein the inner locking mechanism is adapted to prevent premature activation of a needle safety function by an incorrect user operation.

12. The safety device according to claim 11, wherein the inner locking mechanism comprises a snap-in lock between at least two of the at least three independent locking parts in such a manner that the needle shield is locked against movement and the needle is permanently covered by the needle shield.

13. The safety device according to claim 1, wherein the support body is at least partially encased by the needle shield.

14. The safety device according to claim 1, wherein the support body encases at least a portion of a protective needle shield and is connected with the needle shield.

15. The safety device according to claim 1, wherein the two outer locking parts are configured to move telescopically with respect to the middle locking part within an interior region of the middle locking part.

16. The safety device according to claim 15, wherein the two outer locking parts are configured to move telescopically with respect to the middle locking part without moving telescopically with respect to each other.

17. A drug delivery device comprising:
a housing; and
a safety device comprising:
- a support body adapted to receive and hold the drug delivery device,
- a needle shield slidably arranged relative to the support body,
- an inner locking mechanism arranged inside the needle shield between a front end of the needle shield and a front end of the support body and adapted to lock and unlock the needle shield,
- wherein the inner locking mechanism comprises at least three independent locking parts, and
- wherein two outer locking parts of the at least three independent locking parts are telescopically movable relative to a middle locking part of the at least three independent locking parts.

18. The drug delivery device of claim 17, further comprising a pharmaceutically active compound disposed in the housing.

* * * * *

UNITED STATES PATENT AND TRADEMARK OFFICE
CERTIFICATE OF CORRECTION

PATENT NO. : 10,238,809 B2
APPLICATION NO. : 15/105247
DATED : March 26, 2019
INVENTOR(S) : Marc Schader It is certified that error appears in the above-identified patent and that said Letters Patent is hereby corrected as shown below:

On the Title Page

In Column 1 (Assignee), Line 1, delete "Deutchland" and insert -- Deutschland --

In the Specification

In Column 1, Line 8 (approx.), delete "371of" and insert -- 371 of --

Signed and Sealed this
Thirtieth Day of July, 2019

Andrei Iancu
*Director of the United States Patent and Trademark Office*